US012805765B2

(12) United States Patent
Wengarten

(10) Patent No.: US 12,805,765 B2
(45) Date of Patent: Nov. 24, 2026

(54) BIOMETRIC PARAMETER MEASUREMENT

(71) Applicant: CENTERS-SMART LLC, Pomona, NY (US)

(72) Inventor: Yaakov Wengarten, Pomona, NY (US)

(73) Assignee: CENTERS-SMART LLC, Pomona, NY (US)

( * ) Notice: Subject to any disclaimer, the term of this patent is extended or adjusted under 35 U.S.C. 154(b) by 579 days.

(21) Appl. No.: 18/251,090

(22) PCT Filed: Oct. 28, 2021

(86) PCT No.: PCT/US2021/057093

§ 371 (c)(1),
(2) Date: Apr. 28, 2023

(87) PCT Pub. No.: WO2022/094112

PCT Pub. Date: May 5, 2022

(65) Prior Publication Data

US 2023/0397847 A1 Dec. 14, 2023

Related U.S. Application Data

(60) Provisional application No. 63/106,582, filed on Oct. 28, 2020.

(51) Int. Cl.

| | |
|---|---|
| ***A61B 5/145*** | (2006.01) |
| ***A61B 5/00*** | (2006.01) |
| ***A61B 5/024*** | (2006.01) |
| ***A61B 5/026*** | (2006.01) |
| ***A61B 5/1455*** | (2006.01) |

(52) U.S. Cl.
CPC ........ *A61B 5/14532* (2013.01); *A61B 5/0075* (2013.01); *A61B 5/02416* (2013.01); *A61B 5/0261* (2013.01); *A61B 5/1455* (2013.01)

(58) Field of Classification Search
CPC .............. A61B 5/14532; A61B 5/0075; A61B 5/02416; A61B 5/0261; A61B 5/1455; A61B 5/746
See application file for complete search history.

(56) References Cited

U.S. PATENT DOCUMENTS

2004/0068163 A1 4/2004 Ruchti et al.
2008/0119701 A1 5/2008 Milner et al.
(Continued)

OTHER PUBLICATIONS

Extended European Search Report in European Application No. EP 21 88 7537, dated Sep. 6, 2024, 8 pages.
(Continued)

*Primary Examiner* — Abid A Mustansir
(74) *Attorney, Agent, or Firm* — Leason Ellis LLP

(57) ABSTRACT

In the disclosure provided herein, the apparatus, systems and methods describe obtaining biometric measurements, including blood glucose levels, using one or more light sources. In a particular implementation, a biometric parameter measurement system is provided, the system comprising at least one visible light illuminant configured to emit light substantially in the red wavelength and at least one infrared illuminant configured to emit light substantially in the infrared wavelength wherein each of the at least one infrared and visible light illuminants are configured to emit light at a subject.

13 Claims, 6 Drawing Sheets

(56) References Cited

U.S. PATENT DOCUMENTS

| | | | | |
|---|---|---|---|---|
| 2011/0230744 | A1* | 9/2011 | Ribas Ripoll ........ | A61B 5/1455 600/365 |
| 2012/0149997 | A1 | 6/2012 | Diab et al. | |
| 2013/0066172 | A1* | 3/2013 | Kulcke .................. | G01N 21/31 600/310 |
| 2016/0361004 | A1 | 12/2016 | Lange et al. | |
| 2018/0214088 | A1 | 8/2018 | Newberry | |
| 2018/0317821 | A1* | 11/2018 | Arko .................. | A61B 5/14532 |
| 2019/0133471 | A1* | 5/2019 | Olson .................. | A61B 5/0245 |

OTHER PUBLICATIONS

Supplemental European Search Report in European Application No. EP 21 88 7537, dated Sep. 24, 2024, 1 page.

International Preliminary Report on Patentability in corresponding International Application No. PCT/US2021/057093, mailed Feb. 7, 2023.

International Preliminary Report on Patentability in corresponding International Application No. PCT/US2021/057093, mailed May 11, 2023.

* cited by examiner

BIOMETRIC PARAMETER MEASUREMENT

CROSS REFERENCE TO RELATED APPLICATIONS

The present application is a National Stage of International Application No. PCT/US2021/057093, filed Oct. 28, 2021, which claims priority to and the benefit of U.S. patent application No. 63/106,582, filed Oct. 28, 2020, which are incorporated by reference in their entireties. The International Application was published on May 5, 2022 as International Publication No. WO 2022/094112 A1.

FIELD OF THE INVENTION

The present invention is directed to apparatus, systems and methods for monitoring or calculating one or more biometric measurements of a patient.

BACKGROUND OF THE INVENTION

There is often a need to determine the various biometric parameter measurements of a patient. For example, patients suffering from various ailments, such as diabetes etc., require blood glucose level monitoring.

Photoplethysmography (PPG) is a noninvasive, low cost, and simple optical measurement technique applied at the surface of the skin to measure physiological parameters. It is known in the field of biometric parameter measurement to use PPG configurations to obtain pulse oximetry and heart rate calculations for a patient. PPG analysis of patient biometric parameters typically include optical measurements that allow for a subject to have his or her heart rate monitored. Typically, PPG uses non-invasive technology that includes a light source and a photodetector at the surface of skin to measure the volumetric variations of blood circulation. However, PPG devices have several drawbacks, including imprecision in measurements. For example, Fine J, Branan K L, Rodriguez A J, et al. Sources of Inaccuracy in Photoplethysmography for Continuous Cardiovascular Monitoring. Biosensors (Basel). 2021; 11(4):126. Published 2021 Apr. 16. doi:10.3390/bios11040126, herein incorporated by reference in its respective entirety, describes some drawbacks with respect to the present art. While the signals measurement by the currently available PPG devices allow for heart rate estimation and pulse oxymetry readings, it would be beneficial to obtain other important biometric parameters about the health of a subject using non-invasive low-cost approaches.

Thus, what is needed in the art is systems, methods and computer implemented products that are configured to measure a number of biometric parameters sequentially or simultaneously using non-invasive techniques. Furthermore, what is needed in the art is a system, method and computer implemented product that utilizes a plurality of light wavelengths to obtain measurement data from a subject. Additionally, what is needed is the art is one or more biometric parameter measurement devices or systems that can be incorporated into one or more portable form factors, such as watches, bracelets, bands and the like. In a further implementation, what is needed are approaches to transmitting measured biometric parameter data to one or more remote systems for evaluation, monitoring or storage.

Thus, what is needed in the art is a device, system or method that allows for the determination of blood glucose levels without using invasive means or mechanisms and is capable of transmitting or providing this information to remote computers, user or databases.

SUMMARY OF THE INVENTION

In accordance with the disclosure provided herein, the apparatus, systems and methods described are directed to obtaining biometric measurements, including blood glucose levels, using one or more light sources. In a particular implementation, a biometric parameter measurement system is provided. Here, the system comprises at least one visible light illuminant configured to emit light substantially in the red wavelength and at least one infrared illuminant configured to emit light substantially in the infrared wavelength wherein each of the at least one infrared and visible light illuminants are configured to emit light at a subject. The system also includes a light measurement device configured to receive, on a light sensing portion thereof, light produced by each of the at least one infrared and visible light illuminants where the received light has been reflected of of the subject. The biometric parameter measurement system further includes one or more processors having a memory and configured to receive the output signal from the light measurement device based on each of the at least one infrared and visible light illuminants. The biometric parameter measurement system is further configured with one or more processors, configured to execute code therein to calculate a value correlated to the glucose value of the subject. In one or more further implementations, the processor is configured to calculate the glucose value by filtering the signal for each of the at least one infrared and visible light illuminants; generating a heartbeat value using at least one infrared and visible light illuminates; and calculating glucose value for the subject based, at least in part on a difference between the filtered at least one infrared and visible light illuminant signals.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF CERTAIN EMBODIMENTS OF THE INVENTION

By way of overview and introduction, various embodiments of the apparatus, systems and methods described herein are directed towards biometric measurement devises and analysis.

Figure 1:
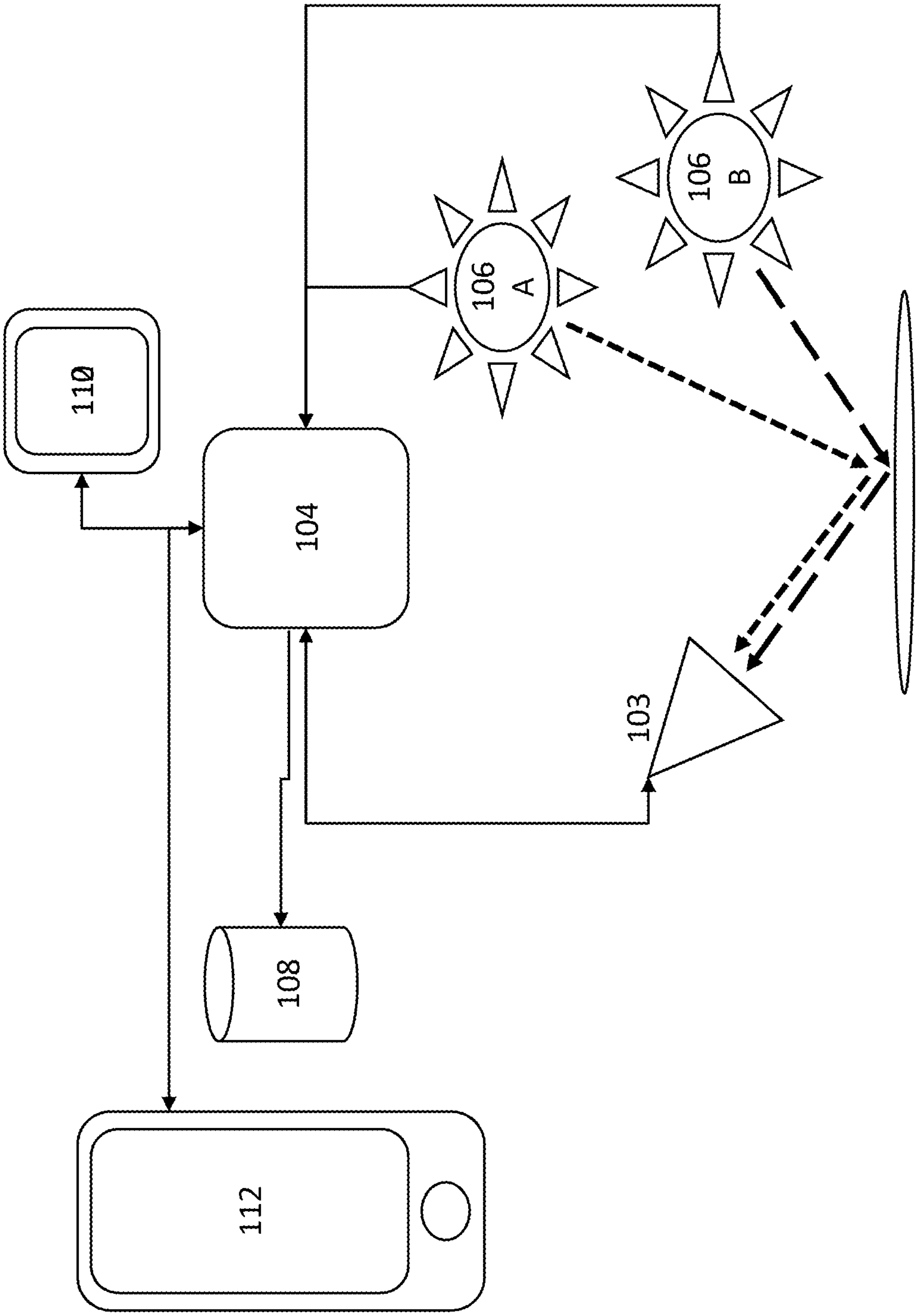
FIG. 1 illustrates devices and components that interface over one or more data communication networks in accordance with one or more implementations of the biometric parameter measurement system.

Referring now to the drawings, in which like references numerals refer to like elements. FIG. 1 illustrates devices and components for obtaining biometric parameter data. In particular, the biometric parameter measurement system described herein in utilizes a plurality of illuminants and a sensor configured to generate output signals in response to receiving light that has been reflected off of a subject 102. As shown, FIG. 1 illustrates a subject 102 under analysis by light measurement device 103, or sensor thereof. Here, the subject 102 can be any individual seeking information about a biometric parameter. For example, the subject 102 is an individual that has exposed his or her skin to the illuminant(s) and sensor configuration described herein. In one or more implementations, the subject 102 is an individual seeking information about the subject's pulse, blood oxygen level, stress level, glucose level or other biometric parameter that can be obtained using PPG techniques.

With continued reference to FIG. 1A, the subject 102 is placed such that the subject 102 can be illuminated by the illuminants described herein. In one or more particular implementations, the subject 102 is positioned within 1-10 centimeters from the illuminant(s) and sensors. For example, the illuminant(s) and sensors are integrated into a watch, band or bracelet worn by the user such that the worn article is in direct contact with the skin of a subject 102.

In a particular implementation, and for ease of explanation with the examples provided herein, the subject 102 is illuminated by two (2) or more different illuminants. In one or more implementations, the illuminant 106A and illuminant 106B are commercially available lighting sources. For instance, the illuminant 106A and illuminant 106B, are separate devices that are configurable to produce a light with certain spectral power distributions and/or wavelengths. For instance, the illuminant 106A and illuminant 106B are one or more discrete light emitting elements, such as LEDs, OLEDs, fluorescent, halogen, xenon, neon. D65 light, fluorescent lamp, mercury lamp. Metal Halide lamp, HPS lamp, incandescent lamp or other commonly known or understood lighting sources. In one arrangement, both illuminant 106A and illuminant 106B are narrow-band LEDs or broad-band LEDs.

In one or more implementations, the illuminants 106A and illuminant 106B include a lens, filter, screen, enclosure, or other elements (not shown) that are utilized in combination with the light source of the illuminant 106A and illuminant 106B to direct a beam of illumination, at a given wavelength or at a range of wavelengths, to the subject 102.

In one implementation, illuminant 106A and illuminant 106B are operable or configurable by an internal processor or other control circuit. Alternatively, illuminant 106A and illuminant 106B are operable or configurable by a processor (either local or remote) or a control device having one or more linkages or connections to illuminant 106A and illuminant 106B. As shown in FIG. 1, illuminant 106A and illuminant 106B are directly connected to a light measurement device 103. Such direct connections can be, in one arrangement, wired or wireless connections.

As further shown in FIG. 1, illuminant 106A and illuminant 106B are positioned relative to the subject 102 and light measurement device 103 so as to provide a 45/0, d/8, or other illumination/pickup geometry combination. However, it will be appreciated that any suitable measurement geometry capable of evaluating light reflected off of the subject 102 is understood and appreciated.

Continuing with FIG. 1, light reflected upon the subject 102 is captured or measured by a light measurement device 103. Here, the light measurement device 103 can be a light measurement device, color sensor or image capture device. For example, the light measurement device 103 is a scientific CMOS (Complementary Metal Oxide Semiconductor), CCD (charge coupled device), colorimeter, spectrometer, spectrophotometer, photodiode array, or other light sensing device and any associated hardware, firmware and software necessary for the operation thereof.

In a particular implementation, the light measurement device 103 is configured to generate an output signal upon light striking the light measurement device 103 or a light sensing portion thereof. By way of non-limiting example, the light measurement device 103 is configured to output a signal in response to light that has been reflected off of the subject 102 and then strikes a light sensor or other sensor element integral or associated with the light measurement device 103. For instance, the light measurement device 103 is configured to generate a digital or analog signal that corresponds to the wavelength or wavelengths of light that impact or are incident upon at least a portion of the light measurement device 103 after being reflected off of the subject 102. In one or more configurations, the light measurement device 103 is configured to output spectral information, RGB information, or another form of single or multi-wavelength data. In one arrangement, the data generated by the light measurement device is representative of light reflected off, or transmitted through, the subject 102.

In one or more implementations, the light measurement device 103 described herein, has one or more optical, NIR or other wavelength channels to evaluate a given wavelength range. In a further implementation, the light measurement device 103 has sufficient wavelength channels to evaluate received light that is in the optical, near infrared, infrared, and ultraviolet wavelength ranges.

In one non-limiting implementation, the light measurement device 103 is integrated or incorporated into a light sensor, camera or image recording device. For example, the light measurement device is included or integrated into a portable electronic device, smartphone, tablet, smartwatch, gaming console, wearable device, cell phone, or other portable or computing apparatus.

The light measurement device 103, in accordance with one embodiment, is a stand-alone device capable of storing local data corresponding to measurements made of the subject 102 within an integrated or removable memory. In an alternative implementation, the light measurement device 103 is configured to transmit one or more measurements to a remote storage device or processing platform, such as processor 104. In configurations calling for remote storage of light measurement data, the light measurement device 103 is equipped or configured with network interfaces or protocols usable to communicate over a network, such as the internet.

Alternatively, the light measurement device 103 is connected to one or more computers or processors, such as processor 104, using standard interfaces such as USB, FIREWIRE, Wi-Fi, Bluetooth, and other wired or wireless communication technologies suitable for the transmission measurement data.

The output signal generated by the light measurement device 103 are transmitted to at least one processor 104 for evaluation as a function of one or more hardware or software modules. As used herein, the term "module" refers, generally, to one or more discrete components that contribute to the effectiveness of the presently described systems, methods and approaches. Modules can include software elements, including but not limited to functions, algorithms, classes and the like. In one arrangement, the software modules are stored as software modules in the memory 205 of the processor 104. Modules, in one or more particular implementations can also include hardware elements substantially as described below.

In one implementation, the processor 104 is located within the same device as the light measurement device 103. However, in another implementation, the processor 104 is remote or separate from the light measurement device 103.

In one configuration, the processor 104 is configured through one or more software modules to generate, calculate, process, output or otherwise manipulate the output signal generated by the light measurement device 103.

In one implementation, the processor 104 is a commercially available computing device. For example, the processor 104 may be a collection of computers, servers, processors, cloud-based computing elements, micro-computing elements, computer-on-chip(s), home entertainment consoles, media players, set-top boxes, prototyping devices or "hobby" computing elements.

Furthermore, the processor 104 can comprise a single processor, multiple discrete processors, a multi-core processor, or other type of processor(s) known to those of skill in the art, depending on the particular embodiment. In a particular example, the processor 104 executes software code on the hardware of a custom or commercially available cellphone, smartphone, notebook, workstation or desktop computer configured to receive data or measurements captured by the light measurement device 103 either directly, or through a communication linkage.

The processor 104 is configured to execute a commercially available or custom operating system, e.g., MICROSOFT WINDOWS, APPLE OSX, UNIX or Linux based operating system in order to carry out instructions or code.

In one or more implementations, the processor 104 is further configured to access various peripheral devices and network interfaces. For instance, the processor 104 is configured to communicate over the internet with one or more remote servers, computers, peripherals or other hardware using standard or custom communication protocols and settings (e.g., TCP/IP, etc.).

The processor 104 may include one or more memory storage devices (memories). The memory is a persistent or non-persistent storage device (such as an IC memory element) that is operative to store the operating system in addition to one or more software modules. In accordance with one or more embodiments, the memory comprises one or more volatile and non-volatile memories, such as Read Only Memory ("ROM"). Random Access Memory ("RAM"), Electrically Erasable Programmable Read-Only Memory ("EEPROM"), Phase Change Memory ("PCM"), Single In-line Memory ("SIMM"), Dual In-line Memory ("DIMM") or other memory types. Such memories can be fixed or removable, as is known to those of ordinary skill in the art, such as through the use of removable media cards or modules. In one or more embodiments, the memory (such as but not limited to memory 205) of the processor 104 provides for the storage of application program and data files. One or more memories provide program code that the processor 104 reads and executes upon receipt of a start, or initiation signal.

The computer memories may also comprise secondary computer memory, such as magnetic or optical disk drives or flash memory, that provide long term storage of data in a manner similar to a persistent memory device. In one or more embodiments, the memory of the processor 104 provides for storage of an application program and data files when needed.

The processor 104 is configured to store data either locally in one or more memory devices. Alternatively, the processor 104 is configured to store data, such as measurement data or processing results, in database 108. In one or more implementations, the database 108 is remote or locally accessible to the processor 104. The physical structure of the database 108 may be embodied as solid-state memory (e.g., ROM), hard disk drive systems, RAID, disk arrays, storage area networks ("SAN"), network attached storage ("NAS") and/or any other suitable system for storing computer data. In addition, the database 108 may comprise caches, including database caches and/or web caches. Programmatically, the database 108 may comprise flat-file data store, a relational database, an object-oriented database, a hybrid relational-object database, a key-value data store such as HADOOP or MONGODB, in addition to other systems for the structure and retrieval of data that are well known to those of skill in the art. The database 108 includes the necessary hardware and software to enable the processor 104 to retrieve and store data within the database 108.

In one implementation, each element provided in FIG. 1 is configured to communicate with one another through one or more direct connections, such as though a common bus. Alternatively, each element is configured to communicate with the others through network connections or interfaces, such as a local area network LAN or data cable connection. In an alternative implementation, the light measurement device 103, processor 104, and database 108 are each connected to a network, such as the internet, and are configured to communicate and exchange data using commonly known and understood communication protocols.

In a particular implementation, the processor 104 is a computer, workstation, thin client or portable computing device such as an Apple iPad/iPhone® or Android® device or other commercially available mobile electronic device configured to receive and output data to or from database 108 and or light measurement device 103.

In one arrangement, the processor 104 communicates with a local display device 110 or a remote computing device 112 to transmit, display or exchange data. In one arrangement, the display device 110 and processor 104 are incorporated into a single form factor, such as a light measurement device that includes an integrated display device. In an alternative configuration, the display device is a remote computing platform such as a smartphone or computer that is configured with software to receive data generated and accessed by the processor 104. For example, the processor is configured to send and receive data and instructions from a processor(s) of a remote computing device. This remote computing device 110 includes one or more display devices configured to display data obtained from the processor 104. Furthermore, the display device 110 is also configured to send instructions to the processor 104. For example, where the processor 104 and the display device are wirelessly linked using a wireless protocol, instructions can be entered into the display device that are executed by the processor. The display device 110 includes one or more associated input devices and/or hardware (not shown) that allow a user to access information, and to send commands and/or instructions to the processor 104 and the light measurement device 103. In one or more implementations, the display device 110 can include a screen, monitor, display, LED, LCD or OLED panel, augmented or virtual reality interface or an electronic ink-based display device.

In a particular implementation, a remote computing device 112 is configured to communicate with the processor 104. For example, the processor 104 is configured to communicate with a smartphone or tablet computer executing a software application configured to exchange data with the processor 104. In one or more implementations, the remote computing device 112 is configured to display data derived or accessed by the processor 104. Here, the remote computing device 112 is configured to execute an application to allow for bi-directional communication with the processor 104. In one or more implementations, the remote computing device 112 is configured to send instructions to initiate the measurement steps provided in steps 202-216 and 502-512 further described herein and receive the data calculated therein.

Those possessing an ordinary level of skill in the requisite art will appreciate that additional features, such as power supplies, power sources, power management circuitry, control interfaces, relays, adaptors, and/or other elements used to supply power and interconnect electronic components and control activations are appreciated and understood to be incorporated.

Figure 2:
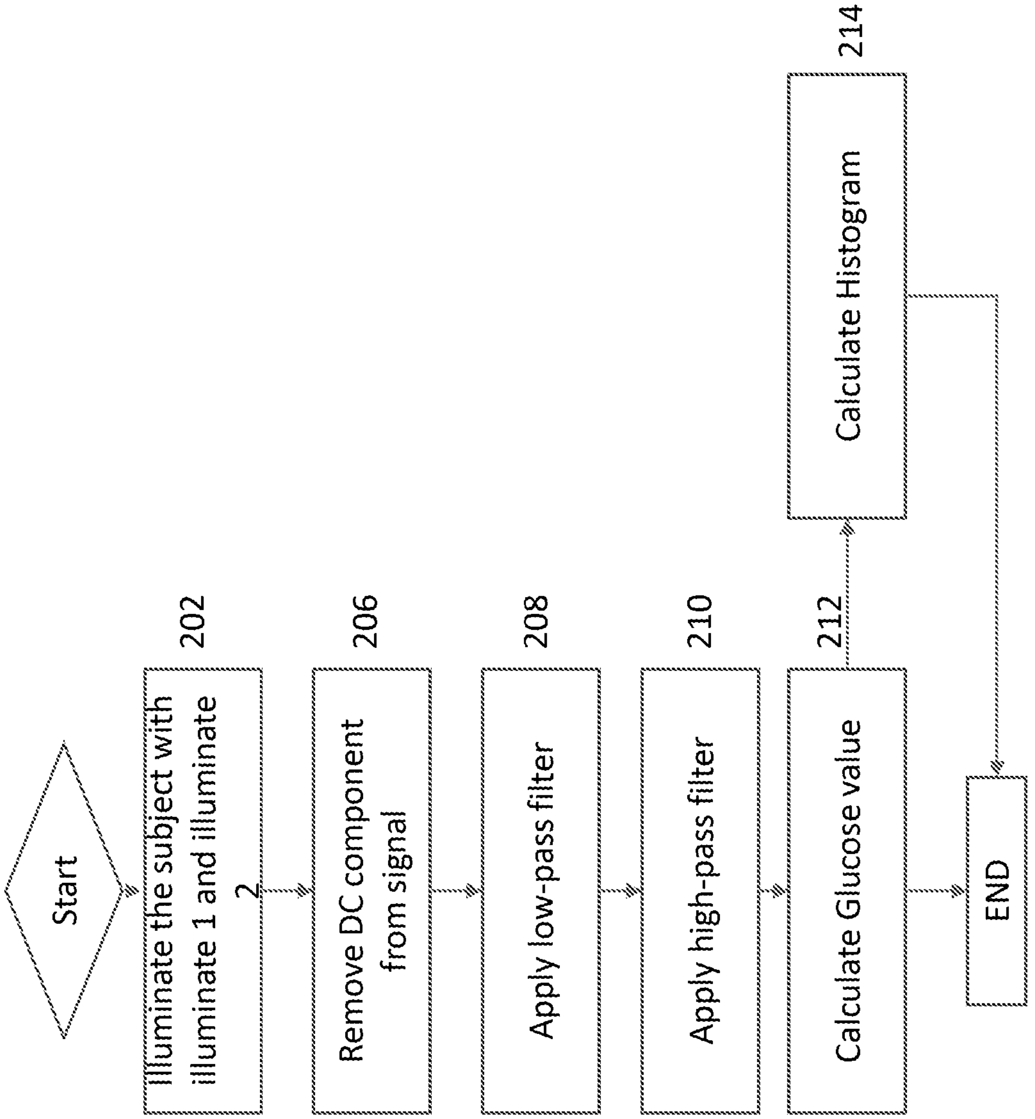
FIG. 2 presents a flow diagram detailing the steps taken in one configuration of the biometric parameter measurement system described herein.
Figure 3:
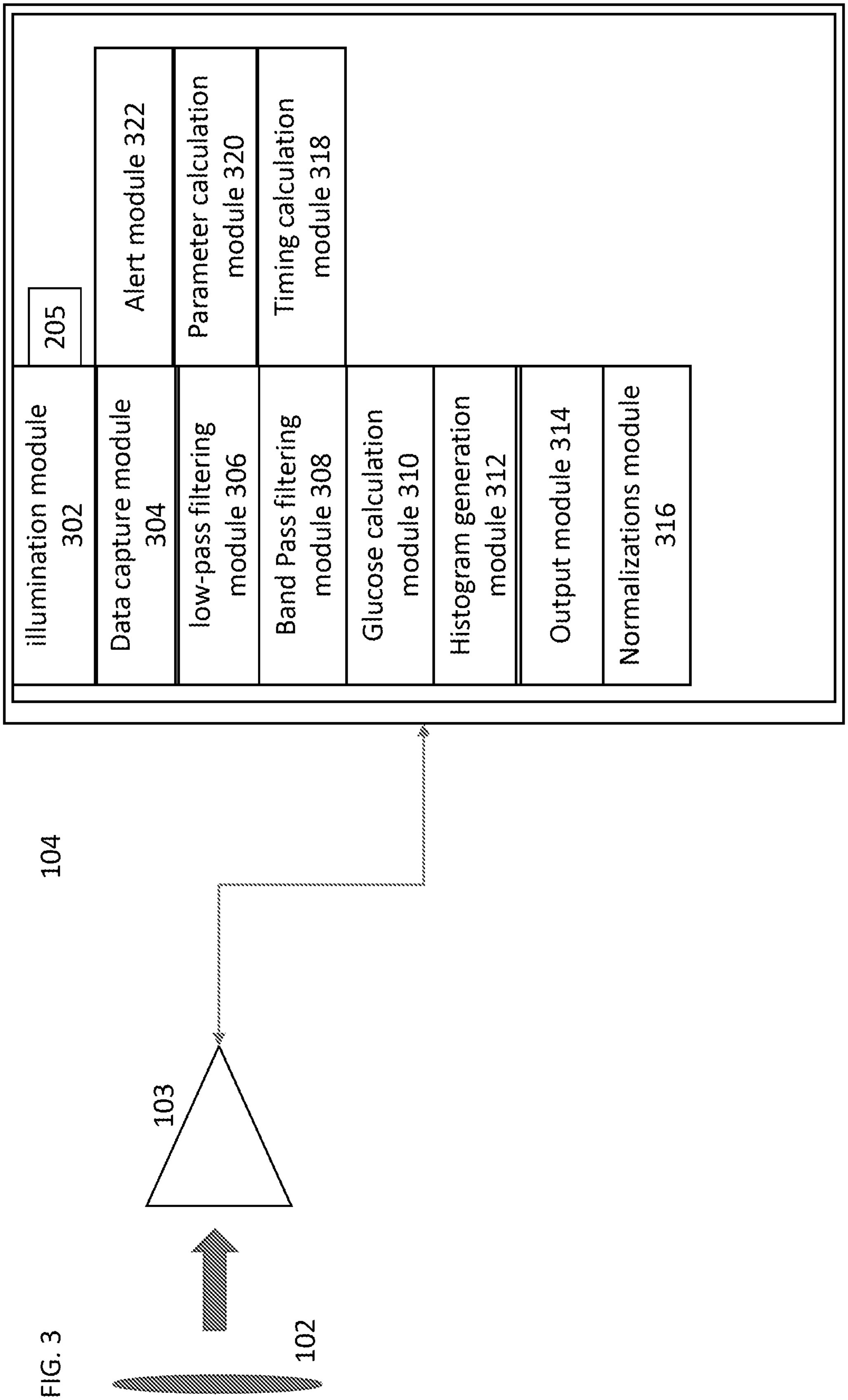
FIG. 3 presents a collection of modules detailing the operative functions of the biometric parameter measurement system according to one configuration.

Turning now to the overview of the operation of the system described in FIGS. 2 and 3, the processor 104 is configured to implement or evaluate the output of the light measurement device 103 in order to determine various biometric parameters of the subject 102.

As shown in illumination step 202, both the infrared illuminant 106A and the red illuminant 106B are configured to illuminate the surface of a subject 103. For example, the illuminate 106A and illuminant 106B are configured as light emitting diodes (LED) that are configurable to emit light within a given frequency range by the processor 104. For example, where the processor 104 is configured by an illumination module 302, a control signal is sent to the illuminant 106A and illuminant 106B that cause them to activate. In one particular implementation, the illuminants are configured to illuminate the subject 102 sequentially. Here, the illumination module causes illuminant 106A to illuminate the subject. Then, once illuminant 106A has been deactivated, the processor 104 configured by the illumination module 302 sends an activation signal to the second illuminant 106B. Where additional illuminants are incorporated (not shown) such additional illuminants are subsequently activated sequentially. In an alternative implementation, where there are two or more illuminants used, each illuminant can be activated simultaneously or in sequence.

Turning now to data collection step 204, once the subject 102 has been illuminated by at least illuminant 106A and illuminant 106B, the light measurement device 103 is configured to output a signal. This signal corresponds to the light received by the light measurement device 103 during the illumination step 202. In one implementation, the signal is waveform data occurring for a particular duration or time interval. For example, the processor 104 is configured by a data collection module 304 to record the signal generated by the light measurement device 103 when infrared light or red LED light has been reflected off of the subject 102 and strikes a sensing element of the light measurement device 103. In one or more implementations, the data collection module 304 includes one or more submodules that are operated to configure the processor 104 to convert the signal received. For example, where the light measurement device 103 is configured to output an analog signal, the submodules of the data collection module configure the processor 104 to convert the analog signals into digital signals prior to further evaluation. Alternatively, where the light measurement device 103 is configured to output a time series or other data value or data objects, the processor 104 is configured by the data collection module 304 to evaluate, normalize or format the raw measurement data generated by the light measurement device 103 prior to use.

By way of general overview, in order to obtain a blood glucose value from the measurement signal, first the DC component of the signal is removed. The remaining AC portion of the signal is subject to a low-pass filter. Next, the signal is subject to a band-pas filter. After the AC signal has been subject to a low-pass and band-pass signal, the glucose value can be generated and a histogram of the data calculated.

Turning now to signal extraction step 206, the AC component of the signal obtained by the light measurement device 103 is isolated. It is understood in the art that the measurements obtained by a light measurement device of a subject can include common pulsatile ("AC") signals. AC, as used herein, refers to a change in a measurement that can be attributed to or associated with changes in arterial blood volume. As the systolic and diastolic pulse travel through an artery or arteriole, the properties of the pulse itself and the compliance of the vessel lead to a change in vessel diameter, leading to a change in blood volume. Such changes correlate with changes in the light detected by a photodiode after illumination. This in turn corresponds to a change in the voltage or current generated by the light measurement device. Additionally, changes in erythrocyte orientation can also lead to changes in optical transmittance, further modifying light detected by a light measurement device as a function of blood volume.

To address this circumstance, an AC extraction module 306 configures the processor 104 to extract the AC signal from the total response value obtained by the light measurement device when the subject 102 was illuminated with illuminant 106A and illuminant 106B. By way of non-limiting example, the AC extraction module 306 configures the processor 104 to extract the AC signals for the response (or output) generated by the light measurement device when illuminated by reflected light from at least illuminant 106A and illuminant 106B according to:

$$w(t)=r(t)+a*w(t-1)$$

$$s(t)=w(t)-w(t-1) \tag{1}$$

Where the values w(t), w(t−1) are intermediate values that are used to represent a history of, or prior values for the DC signal. Here, the DC signal represents the total response signal or waveform with the AC component removed. Here, r(t) represents the current input signal at time t and a is the filter's scale factor, (such that it defines a filter band). In one arrangement, the value for a is a constant. For example, the value for a is less than 1. By way of further example, the value for constant "a" is 0.95. In the above equation, s(t) refers to the DC remover output signal at time t. [VS1]

Turning now to filtering step 208, each of the AC extracted values $S_{RED}$ and $S_{IR}$ are evaluated using a low pass filter. For example, the filtering module 308 configures the processor 104 to remove high frequency signals from the $S_{RED}$ and $S_{IR}$ values obtained in extraction step 206. In one particular implementation, high frequency noise is removed from the $S_{RED}$ and $S_{IR}$ values. For example, a low pass Butterworth filter is applied to the AC signal according to:

$$y(t)=a*x(t)+b*x(t-1) \tag{2}$$

where x(t)) input signal, a≈0.086 and b≈0.827 for first order infinite impulse response (IIR) filter with 3 Hz cut frequency.

As used here, x(t) is the low pass filter input signal at time t. Here, the values for a and b are constants. For example, a=0.086, b=0.827 and each represent coefficients of an IIR low pass filter. In one or more alternative implementations, the values for a and b can be altered. Additionally, y(t) corresponds to the low pass filter output signal at time t. Similarly, the 3 Hz cut frequency for the can also be adjusted depending on the specific circumstances encountered.

Turning now to a bandpass filtering step 210, the processor is configured to filter the signal obtained in the first filtering step. For example, the bandpass filtering module 310 configures the processor 104 to apply a band-pass filter to the signal obtained in the filtering step 208. In one or more further implementations, the bandpass filtering step 210 includes one or more sub-steps directed to acquiring the heartbeat of the subject 102. For example, a bandpass filtering module 310 configures a processor to extract heartbeat data from the subject 102 using the low-pass filtered $S_{RED}$ and $S_{IR}$ values. In one configuration, the raw values for $S_{RED}$ and $S_{IR}$ are used to calculate a heartbeat. Once the interval of a heartbeat for the subject is established, the $S_{RED}$ and $S_{IR}$ signals that have been filtered according to filtering step 208 are then subsequently filtered in bandpass filtering step 210. For example, a bandpass Butterworth filter is used to remove noise from the previously filtered signal according to:

$$v(t)=k1*y(t)+k2*v(t-1)+k3*v(t-2)$$

$$z(t)=v(t)+v(t-2)-2v(t-1), \qquad (3)$$

where y(t) input signal, k1≈0.901, k2≈1.793 and k3≈0.812 for second order HR filter with low frequency 2.35 Hz and high frequency 6 Hz.

Here, y(t) corresponds to band pass filter input signal at time t. The values for k1, k2, k3 are coefficients of UR band pass filter. Furthermore, v(t), v(t−1), v(t−2) represent intermediate filter values at time t, t−1, t−2, such that these values represent a filter's history. Here, z(t) represents the band pass filter output signal at time t.

As with filtering step 208, it will be appreciated that the values for k1, k2, and k3 can be adjusted based on the specific circumstances of the bandpass filter, the subject 103, or processor 104. Furthermore, the frequency range for the band can be adjusted so as to have a frequency range greater than 2.35 to 6 Hz. In one or more alternative arrangements, the lower boundary of the band is greater or less than 2.35 Hz. In a further arrangement, the upper boundary of the band is greater or less than 6 Hz.

As shown in glucose calculation step 212, once the $S_{RED}$ and $S_{IR}$ signals have been passed through the first and second filtering steps (208-210), the filtered values can then be used to calculate the glucose values for the subject 102. For example, a glucose calculation module 310 configures the processor 104 to use the filtered values for $S_{RED}$ and $S_{IR}$ signals and obtain the difference between the signals. The difference between the measured, filtered signals corresponds to the glucose value. In one particular implementation, the difference between the $S_{RED}$ and $S_{IR}$ signals can be used to determine the glucose value of a subject 102 according to:

$$\text{value}_i = z(t),\ i = t,\ x = s_{ir} - s_{red}$$

$$\text{rmsValue}_k = \frac{1}{2} * \sqrt{\frac{\sum_{i=k-N}^{k} \text{value}_i^2}{N}}$$

$$\text{glucose} = 0.05 * \text{rmsValue} + 4.5$$

By way of further example, the following can be used to obtain an input signal for the glucose calculation:

$$x'(t)=s_{ir}(t)-s_{red}(t)$$

Where:

$S_{ir}(t)$—is the value of input Infrared signal;

$s_{red}(t)$—is the value of input Red signal;

x'(t)—is the input signal for glucose calculation; and t—is the number of input signal sample (equivalent of time).

To make a low pass and band pass filtration of $x'^{(t)}$, it is implemented as x(t) in formulas (2) and (3). As result of this filtering the band pass filter output signal corresponds to z'(t). Thus, the value the floating RMS can be obtained using z'(t) according to:

$$\text{rmsValue}(t) = \frac{1}{2} * \sqrt{\frac{\sum_{i=t-N}^{t} z'(i)}{N}}$$

where N=200—which corresponds to the floating window size.

Figure 6:
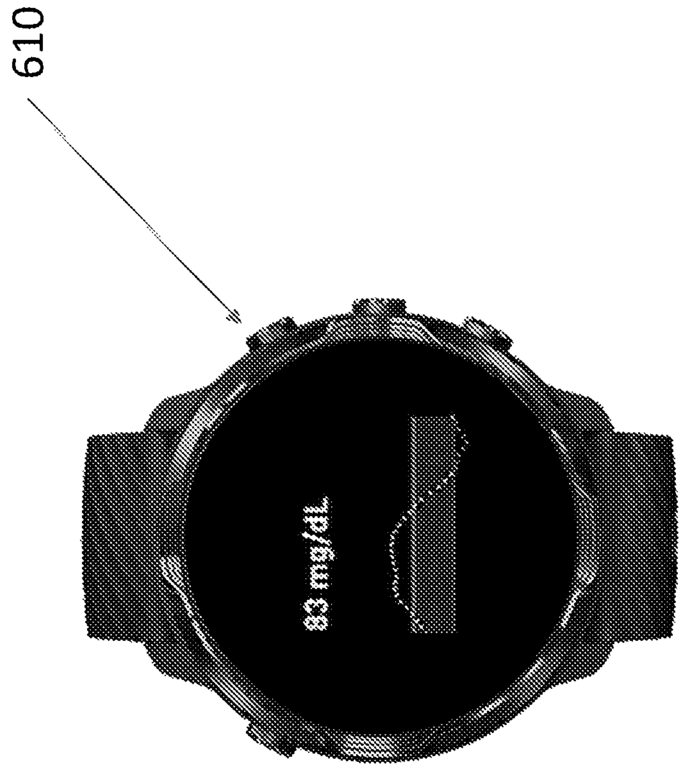
FIG. 6 is one configuration of the biometric parameter measurement device described herein depicting a measurement of a biometric parameter.

Using this approach, the glucose level value can be calculated using the following formula:

$$\text{glucose}(t)=0.05*\text{rmsValue}(t)+4.5$$

where glucose(t) is current glucose level in mmol/L. For example, FIG. 6 is one configuration of the biometric parameter measurement device described herein depicting a measurement of a glucose measurement provided on a display device 110. In this configuration, the processor 104, light measurement device, and illuminants, are integrated into a wearable device 610.

As shown in histogram step 214, once the glucose value has been calculated using the heart beat data, a histogram can be generated for display to a user. For example, the output module 314 configures the processor 104 to output the glucose data and time interval data for the purposes of generating a histogram relating to the derived glucose value of the subject 102.

Returning now to step extraction step 206, once the DC component of the $S_{RED}$ and $S_{IR}$ signals has been removed, the AC component can also be used to determine additional biometric values for the subject 102. For example, a subject's pulse, blood pressure and stress values can be calculated using the $S_{RED}$ and $S_{IR}$ values.

Figure 5:
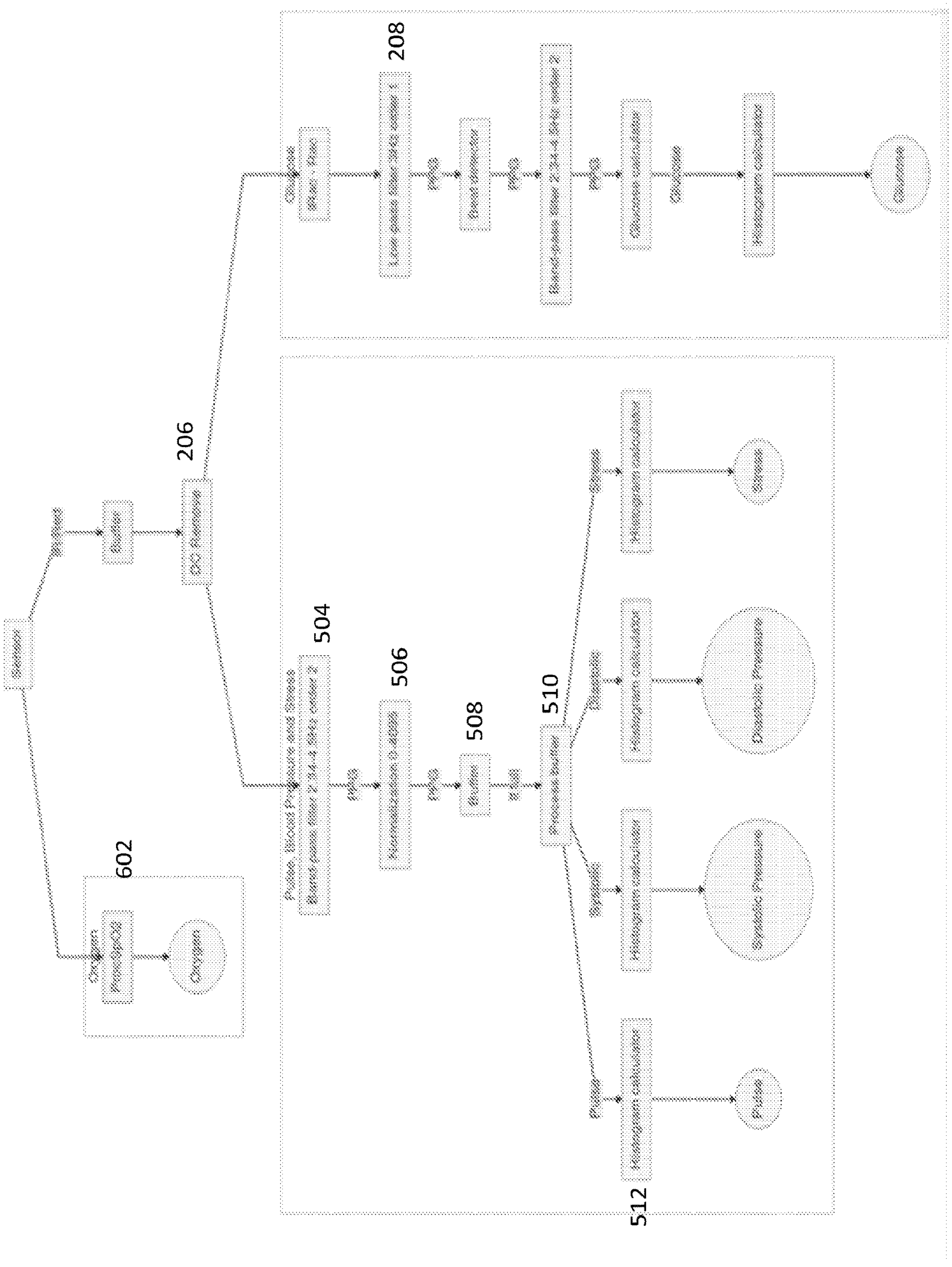
FIG. 5 is a flow diagram detailing the determination of biometric parameters of a subject by the biometric parameter measurement system provided herein.

As shown of FIG. 5, the $S_{RED}$ and $S_{IR}$ values determined in extraction step 206 can also be used to determine the pulse, blood pressure, and stress values of a subject 102 by filtering the extracted $S_{RED}$ and $S_{IR}$ to according to filtering step 504. In one implementation, the filtering step 504 filters the $S_{R}e$ and $S_{IR}$ signals using a band-pass filter. For example, the band pass filtering module 308 configures a processor 104 to evaluate the AC isolated response values for $S_{RED}$ and $S_{IR}$ using the same band pass filter configuration as provided for in bandpass filtering step 210. In an alternative configuration, the values used in bandpass filter step 201 are changed when the band-pass filter is used in filtering step 504. Where the heartbeat of a subject 102 has not yet been determined, the filtering step 504 includes one or more sub-steps directed to acquiring the heartbeat of the subject 102. For example, a bandpass filtering module 310 configures a processor 104 to extract heartbeat data from the low-pass filtered $S_{RE}$ and $S_{IR}$ values. Alternatively, the raw values for $S_{RED}$ and $S_{IR}$ are used to calculate a heartbeat. In a further implementation, the timing interval data corresponding to the heartbeat of the subject 102 is accessed from the memory 105 of the processor for use. For example, where band pass filtering step 210 has already determined the heartbeat of the subject, such heartbeat data is stored in a memory for access by the processor in filtering step 504. Once the interval of a heartbeat for the subject 102 is established or acquired, the $S_{RED}$ and $S_{IR}$ signals that have been filtered according to filtering step 208 are then subsequently filtered in bandpass filtering step 210 according to:

$$v(t)=k1*y(t)+k2*v(t-1)+k3*v(t-2)$$

$$z(t)=v(t)+v(t-2)-2v(t-1), \tag{3}$$

where y(t) input signal, k1≈0.901, k2≈1.793 and k3≈0.812 for second order IIR filter with low frequency 2.35 Hz and high frequency 6 Hz.

However, in an alternative implementation, the filtered values for $S_{RED}$ and $S_{IR}$ obtained in step bandpass filtering 210 can be stored in one or more memories of the processor 104 for retrieval and usage. For example, in an alternative implementation, the processor 104 is configured by the bandpass filtering module 310 to store the filtered signals in bandpass filtering step 210 and provide the stored filtered signal values for further use in filtering step 504. As with bandpass filtering step 210, in filtering step 504, it will be appreciated that the values for k1, k2, and k3 can be adjusted based on the specific circumstances. Furthermore, the frequency range for the band can be adjusted so as to have a frequency range greater than 2.35 to 6 Hz. In one or more alternative arrangements, the lower boundary of the band is greater or less than 2.35 Hz. In a further arrangement, the upper boundary of the band is greater or less than 6 Hz.

Next, a normalization step 506 normalizes the signal obtained in the parameter filtering step 502. For example, the processor 104 is configured by a normalization module 316, or submodules thereof, to normalize the signal within a range of [0-4095]. However, in alternative configurations the normalization module 316 configures the processor 104 to adjust the normalization range to be greater or smaller than [0-4095].

Figure 4:
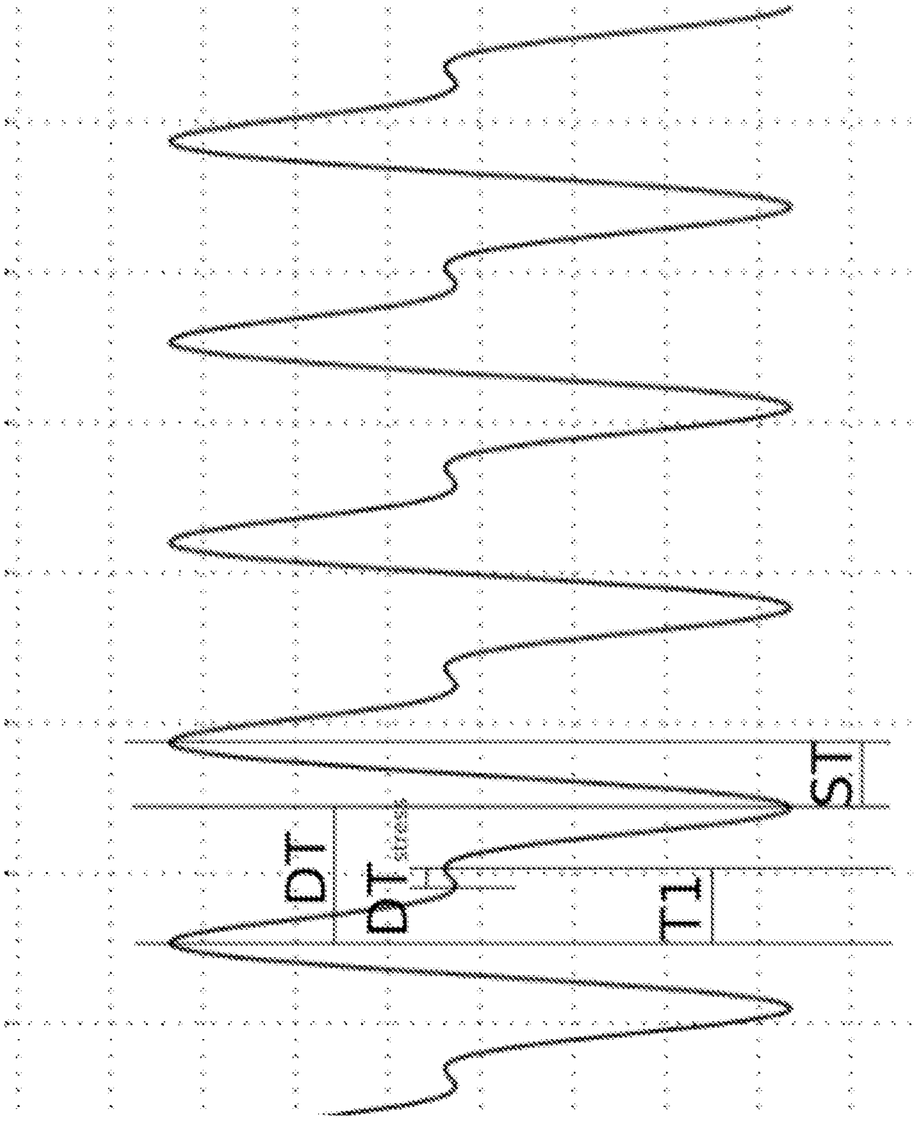
FIG. 4 is a graph detailing the waveform analyzed according to the biometric parameter measurement system provided herein.

As shown in timing calculation step 508, time interval values for the $S_{RED}$ and $S_{IR}$ measurements obtained are derived from the AC extracted form of the signals $S_{RED}$ and $S_{IR}$. For example, a timing module 318 configures the processor 104 to generate time data from the $S_{RED}$ and $S_{IR}$ signals. In one particular implementation, the time data is calculated by analyzing the relative peaks of the signal data. For example, FIG. 4 provides a waveform of a signal generated by the light measurement device 103 in response to a measurement of either red or infrared light. As shown in FIG. 4, the signal provided by the light measurement device incudes a first and second peak. The processor 104 is configured by the timing module 318 to determine diastole and systole time using the measured peaks of the waveform according to the following:

DT Diastole time (1 s measuring between second pulse start and first pulse peak: $\Delta t_D=t_{j+1}-t_i$, where $t_{j+1}$—second pulse start and $t_i$—first pulse peak.

ST Systole time is measuring between second pulse peak and second pulse start: $\Delta t_S=t_{i+1}-t_{j+1}$, where $t_{i+1}$—second pulse peak.

T1 Time between first systole(pulse) and diastole peaks: $\Delta t_1=t_k-t_i$, where $t_k$—first diastole peak.

DT(stress) Diastole time is measuring between diastole peak and pulse note: $\Delta t_D s=t_k-t_n$, where $t_n$—first pulse notch.

Using the timing interval data obtained in timing calculation step 508, biometric parameter data can be obtained as in parameter calculation step 510. For example, the processor 104 is configured by a parameter calculation module 320 to determine the pulse of a subject using the $S_{RED}$ and $S_{IR}$ values processed according to steps 502-510. In one implementation the pulse (heart rate) of a subject 102 is calculated according to:

$$H=\frac{60}{t_{i+1}-t_i},$$

where H—heart rate (pulse).

In a further implementation, the timing data can also be used to obtain the blood pressure (both systolic and diastolic) of the subject according to:

$$P_S=-0.879\Delta t_D+183.46,$$

$$P_D=-0.3449\Delta t_1+174.64$$

where $P_S$—systole blood pressure and $P_D$ diastole blood pressure.

Furthermore, a stress parameter for the subject can be calculated according to the following:

$$S=-0.2\Delta t_D s+160,$$

where S—stress level, S∈[0; 100]

In each of the proceeding parameter calculations, the processor is further configured by the histogram calculation module to calculate histogram for each of the pulse, systolic, diastolic, stress parameters of the subject. For example, a histogram calculation module 312 configures the processor as shown in step 512. Here, histogram values are generated and output as representative of the parameter values derived from the measurements of the subject 102.

In yet a further implementation, the blood oxygen value for the subject can be calculated according to a blood oxygen calculation step using the response values for $S_{RED}$ and $S_{IR}$ values. As shown with respect to step 602, the processor 104 is configured to use the $S_{RED}$ and $S_{IR}$ values to calculate a blood oxygen saturation level. For example, the processor 104 is configured by a blood oxygen module 324 to access the raw AC extracted values for $S_{RED}$ and $S_{IR}$ and calculate the blood oxygen level for a subject according to:

$$a_{ir}=\log r_{ir}(t)$$

$$a_{red}=\log r_{red}(t)$$

$$Hb_O=\frac{0.1924403a_{red}-0.7925498a_{ir}}{-0.199}$$

$$Hb=\frac{0.2760284a_{red}-0.102465a_{ir}}{0.199}$$

-continued $$Hb_t = Hb_O + Hb$$

$$SpO_2 = \frac{Hb_O}{Hb_t} + 20$$

The generated biometric parameters for the patient can be output by the processor 104 configured by the output module 314 to output the generated biometric parameters to an output or display device for further use. In one arrangement, both the glucose value and the biometric parameters are output to a remote database, such as database 108 for further processing and analysis. Alternatively, the glucose and biometric parameters are output to a display device 110, such as a smartphone or other device for display to a user. In yet a further implementation where a display device, such as an LCD display, is provided in a form factor with the processor, light measurement device and illuminants, the output module 314 configures the processor 104 to output the glucose and biometric parameters to the associated or integrated display, as shown in FIG. 6.

In one or more further implementations the illuminant 106A and illuminant 106B, the light measurement device 103, processor 104 and an integrated display device are incorporated into single form factor. In one particular implementation, the form factor is a watch or other wearable device configured to rest upon the skin of the subject 102 and provide periodic or continuous monitoring of the glucose and other biometric parameters.

In a particular implementation, the processor 104 is configured with an alert module 322, or submodule % thereof. The alert module 322 configures the processor 104 to periodically obtain glucose values and biometric parameters of the subject 102 and compare the derived values to one or more pre-determined values or thresholds. Where the glucose values or biometric parameters exceed the predetermined threshold (or fall below a predetermined threshold), an alert message is generated. In one or more implementations, an audible alarm or alert is generated by audio device connected to the processor 104. For example, where one or more speakers are configured to communicate with the processor 104, the speakers are sent an alert signal or sound to alert the subject 102 that the threshold has been exceeded. Likewise, the alert module is configured to communicate with one or more remote databases or computers 112. Here the remote computers 112 or monitors are provided by a health care provider. In this configuration, where the glucose values or biometric parameters are evaluated by a remote computer system, alerts can be generated and sent to one or more additional computers. For example, where the subject is a student, the biometric parameter measurement system described can be configured to alert a parent or guardian, school official or on-site medical care professional that the subject's biometric parameters have exceed a pre-set threshold.

While this specification contains many specific embodiment details, these should not be construed as limitations on the scope of any embodiment or of what can be claimed, but rather as descriptions of features that can be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements. Also, the phraseology and terminology used herein is for the purpose of description and should not be regarded as limiting. The use of "including," "comprising." or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems cited throughout this application are incorporated by reference herein. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those claims, and by equivalents of such features.

What is claimed is:

1. A biometric parameter measurement system comprising:

at least one visible light illuminant configured to emit light substantially in the visible wavelength;

at least one infrared illuminant configured to emit light substantially in the infrared wavelength;

wherein each of the at least one infrared and visible light illuminates are configured to emit light at a subject;

a light measurement device configured to receive, on a light sensing portion thereof, light produced by each of the at least one infrared and visible light illuminates and has been reflected off of the subject and generate a response output signal in response thereto;

one or more processors having a memory and configured to receive the output signal from the light measurement device based on each of the at least one infrared and visible light illuminants; and calculate a value correlated to a glucose value of the subject by filtering the signal for each of the at least one infrared and visible light illuminants to isolate an AC component of a measurement value;

at least one additional visible illuminant that is configured to generate a light in a wavelength different than the visible light illuminant; and where calculating the glucose value further includes obtaining a low pass and band pass filtration of $x'^{(t)}$, to obtain a filter output signal—z'(t) and a floating RMS value according to:

$$\mathrm{rmsValue}(t) = \frac{1}{2} * \sqrt{\frac{\sum_{i=t-N}^{t} z'(i)}{N}}$$

where N=200—which corresponds to the floating window size, and i=t.

2. The biometric parameter measurement system of claim 1, wherein the AC component of the measurement value corresponds to a variation in measurement values associated with arterial blood volume of the subject.

3. The biometric parameter measurement system of claim 1, wherein the filtering of the signal for each of the at least one infrared and visible light illuminants each signal includes: generating a heartbeat value using at least one infrared illuminant and at least one visible light illuminant;

providing a second filtering of the of the filtered at least one infrared and visible light illuminants; and calculating glucose value for the subject based, at least in part on a difference between the filtered at least one infrared and visible light illuminant signals.

4. The system of claim 1, wherein the visible light illuminant is configured to emit light substantially in the red wavelength.

5. The system of claim 1, wherein the visible and infrared light illuminants are a single broad-band illuminant.

6. The system of claim 1 wherein calculating the glucose value includes calculating the following:

$$x'(t)=S_{ir}(t)-S_{red}(t)$$

Where:

$S_{ir}(t)$—is the value of input Infrared signal $S_{red}(t)$—is the value of input visible light signal x'(t)—is the input signal for glucose calculation t—is the number of input signal sample (equivalent of time).

7. A method for determining at least one biometric parameter measurement of the subject, the method comprising:

measuring, with a light measurement device, light emitted from at least one visible light illuminant and reflected off of the subject;

measuring, with the light measurement device, light emitted from at least at least one infrared illuminant and reflected off of the subject and generate a response output signal in response thereto; calculating, using a processor configured by code executing therein, a value correlated to a glucose value of the subject by filtering the signal for each of the at least one infrared and visible light illuminants to isolate an AC component of a measurement value, wherein the AC component of the measurement value corresponds to a variation in measurement values associated with arterial blood volume of the subject, and wherein calculating the glucose value includes calculating the following:

$$x'(t)=S_{ir}(t)-S_{red}(t)$$

Where:

$S_{ir}(t)$—is the value of input Infrared signal $S_{red}(t)$—is the value of input visible light signal x'(t)—is the input signal for glucose calculation t—is the number of input signal sample (equivalent of time), where calculating the glucose value further includes obtaining a low pass and band pass filtration of x'(t), to obtain a filter output signal—z'(t) and a floating RMS value according to:

$$\mathrm{rmsValue}(t) = \frac{1}{2} * \sqrt{\frac{\sum_{i=t-N}^{t} z'(i)}{N}}$$

where N=200—which corresponds to the floating window size, and i=t.

8. The method of claim 7, wherein calculating the glucose value includes:

generating a heartbeat value using at least one infrared illuminant and at least one visible light illuminant;

providing a second filtering of the of the filtered at least one infrared and visible light illuminants; and calculating glucose value for the subject based, at least in part, on a difference between the filtered at least one infrared and visible light illuminant signals.

9. The method of claim 7, wherein the visible light illuminant is configured to emit light substantially in the red wavelength.

10. The method of claim 8, wherein the visible and infrared light illuminants are a single broad-band illuminant.

11. The method of claim 7, further comprising at least one additional visible illuminant that is configured to generate a light in a wavelength different that the visible light illuminant.

12. The method of claim 7, where calculating the glucose value, glucose (t) includes calculating $$\mathrm{glucose}(t)=0.05*rms\mathrm{Value}(t)+4.5$$

where glucose(t) is current glucose level in mmol/L.

13. A biometric parameter measurement system comprising:

at least one visible light illuminant configured to emit light substantially in the visible wavelength;

at least one infrared illuminant configured to emit light substantially in the infrared wavelength;

wherein each of the at least one infrared and visible light illuminates are configured to emit light at a subject;

a light measurement device configured to receive, on a light sensing portion thereof, light produced by each of the at least one infrared and visible light illuminates and has been reflected off of the subject and generate a response output signal in response thereto;

one or more processors having a memory and configured to receive the output signal from the light measurement device based on each of the at least one infrared and visible light illuminants; and calculate a value correlated to a glucose value of the subject by filtering the signal for each of the at least one infrared and visible light illuminants to isolate an AC component of a measurement value; at least one additional visible illuminant that is configured to generate a light in a wavelength different than the visible light illuminant; and where calculating the glucose value, glucose (t) includes calculating:

$$\text{glucose}(t)=0.05*rms\text{Value}(t)+4.5$$

where glucose (t) is current glucose level in mmol/L.

* * * * *